United States Patent [19]

Rupich

[11] Patent Number: 5,064,516
[45] Date of Patent: Nov. 12, 1991

[54] MEASURING GAS LEVELS

[75] Inventor: Martin W. Rupich, Framingham, Mass.

[73] Assignee: Gas Research Institute, Chicago, Ill.

[21] Appl. No.: 211,576

[22] Filed: Jun. 27, 1988

Related U.S. Application Data

[62] Division of Ser. No. 75,243, Jul. 16, 1987.

[51] Int. Cl.$^5$ ............................................. G01N 27/26
[52] U.S. Cl. ........................... 204/153.1; 204/153.17; 204/400; 204/412; 204/415; 204/432
[58] Field of Search .................... 204/1 TK, 402, 415, 204/432, 400, 153.1, 153.17

[56] References Cited

U.S. PATENT DOCUMENTS

| | | | |
|---|---|---|---|
| 3,272,725 | 9/1966 | Garst | 204/415 |
| 3,454,485 | 7/1969 | Hauk et al. | 204/415 |
| 3,776,832 | 12/1973 | Oswin | 204/195 |
| 3,852,169 | 12/1974 | Kring et al. | 204/1 K |
| 3,880,722 | 4/1975 | Beltzer | 204/1 K |
| 4,036,724 | 7/1977 | Binder et al. | 204/1 K |
| 4,057,478 | 11/1977 | Bruckenstein et al. | 204/415 |
| 4,233,031 | 11/1980 | Matson et al. | 204/412 |
| 4,406,770 | 9/1983 | Chan et al. | 204/415 |
| 4,508,598 | 4/1985 | Giner | 204/1 T |
| 4,566,949 | 1/1986 | Berger | 204/402 |
| 4,614,577 | 9/1986 | Mund et al. | 204/415 |
| 4,729,824 | 3/1988 | Giner | 204/415 |
| 4,735,691 | 4/1988 | Green et al. | 204/402 |

FOREIGN PATENT DOCUMENTS 1531761 11/1978 United Kingdom ............... 204/402

OTHER PUBLICATIONS

Wojciechowski, "Square-Wave Anodic Stripping Analysis in the Presence of Dissolved Oxygen," Anal. Chem. 57:155-158 (1985).
Wang et al., "Subtractive Anodic Stripping Voltammetry with Flow Injection Analysis," Anal. Chem. 56:156-159 (1984).
Bond, "Polarographic Procedures Without Removal of Oxygen, and Other Approaches to Making the Determinations More Rapidly," Talanta 20: 1139-1152 (1973).
Batley, "In Situ Electrodeposition for the Determination of Lead and Cadmium in Sea Water," Analytica Chimica Acta, 124: 121-129 (1981).
Wang, J., Stripping Analysis Principles, Instrumentation and Applications, VCH Publishing Inc., Deerfield Beach, 1985.
LaConti et al., J. Electrochem. Soc. 118: 506-510 (1971), ("Electrochemical detection of $H_2$, CO, and hydrocarbons in inert or oxygen atmospheres").
Blurton et al., J. Electrochem. Soc. 121: 1315-1317 (1974), ("The electro-oxidation of carbon monoxide on platinum").
Gilman, J. Phys. Chem., vol. 67, p. 78 (1963), ("A study of the mechanism of carbon monoxide adsorption on platinum by a new electrochemical procedure").
Breiter, Proc. Symp. on Electrocatalysis 82: 102–109 (1982), ("Study of involving reactions at potentials of the hydrogen region in acid solution on smooth and platinized platinum by $CO_{ad}$").

Primary Examiner—T. Tung
Attorney, Agent, or Firm—Fish & Richardson

[57] ABSTRACT

A method for measuring the amount of an electroactive gas in a gaseous mixture using an electrochemical cell, the cell including a working electrode (anode), counter electrode (cathode), an electrolyte in which oxygen reduction is inhibited, means for applying a variable potential across the electrodes, and means for measuring current flow between the electrode, the method involving contacting the gaseous mixture with the anode, applying a potential across the anode and cathode and cycling the applied potential between a potential level at which the gas in the gaseous mixture adsorbs onto the anode and a potential level at which the adsorbed gas in the gaseous mixture is oxidized, and measuring the current resulting from the anodic sweep portion of the potential cycle as a measure of the amount of the adsorbed gas in the gaseous mixture.

10 Claims, 2 Drawing Sheets

MEASURING GAS LEVELS

This is a divisional of copending application Ser. No. 075,243 filed on July 16, 1987.

BACKGROUND OF THE INVENTION

The invention relates to measuring gas levels using an electrochemical cell.

In such measurements, the air containing the gas to be measured is brought into contact with the cell, which contains at least an anode and a cathode and preferably also a reference electrode in contact with an electrolyte. The gas diffuses through the thin layer of electrolyte covering the anode and adsorbs onto the anode as the potential applied between the anode and cathode or reference electode is maintained at a constant level. Typically, the steady state current resulting from the reaction of the gas at the anode surface is measured to determined the amount of the gas present.

LaConti and Maget, J. Electrochem. Soc., Vol. 118, p. 506 (1971), discloses a platinum gas diffusion (fuel cell type) electrode (anode) sprayed onto the surface of a solid polymer electrolyte, including sulfonated fluorinated hydrocarbon as a carbon monoxide (CO) detector. The lower limit of the operating range of the electrode is 0.71V vs. RHE (reversible hydrogen electrode).

Blurton and Sedlack, J. Electrochem. Soc., Vol. 121, p. 1315 (1974), discloses a platinum gas diffusion electrode in sulfuric acid, operating in a range of 0.9V to 1.5V vs. RHE, measuring steady state CO oxidation currents and using an internal reference electrode.

Oswin, U.S. Pat. No. 3,776,832, describes an electrochemical cell used for detection of noxious gases which includes an anode, a cathode, and a reference electrode in an aqueous electrolyte. A fixed potential is maintained between the anode and the reference electrode; the gas reacts at the anode and the resulting current is measured to determine the amount of the gas present in the sample. For CO measurements, the anode, cathode and reference electrodes are platinum/Teflon diffusion electrodes, and sulfuric acid is used as the electrolyte. The cell operates within the range of 0.9V to 1.5V vs. RHE.

The methods of LaConti et al., Blurton et al., and Oswin all rely on restricting the potential range of their potentiostatic electrodes to potentials where the current due to oxygen reduction and to oxygen evolution (oxygen interference) is negligible.

Stripping voltammetry is an alternative method, and a more sensitive one, for measuring the concentration of an electroactive species in a gas in contact with an electrode. Gilman, J. Phys. Chem., Vol. 67, p. 78 (1963) demonstrated this technique for measuring CO in an inert gas. The technique consists of allowing the active component, for example CO, to adsorb on the electrode at a potential where it does not oxidize and then anodically sweeping the potential and measuring the current resulting from oxidation of the adsorbed gas.

Although stripping voltammetry has many advantages over the steady state method, it could not be applied to the quantitative measurement of CO or other electroactive gaseous species in air because of interference by reduction of oxygen at the adsorbing potentials. For example, Breiter, Proc. Symp. on Electro-catalysis, Vol. 82-2, p. 102 (1982), has shown that reduction of oxygen removes CO adsorbed on a platinum electrode.

The present invention discloses formulations of electrolytes which permit the use of stripping voltammetry even when oxygen is present in the gaseous mixture.

SUMMARY OF THE INVENTION

The present invention features a method for measuring the amount of an electroactive gas in a gaseous mixture using an electrochemical cell, the cell including a working electrode (anode), counter electrode (cathode), an electrolyte in which oxygen reduction is inhibited, means for applying a variable potential across the electrodes, and means for measuring current flow between the electrodes, the method involving contacting the gaseous mixture with the anode, applying a potential acoss the anode and cathode and cycling the applied potential between a potential level at which the gaseous mixture adsorbs onto the anode and a potential level at which the adsorbed mixture is oxidized, and measuring the current resulting from the anodic sweep portion of the potential cycle as a measure of the amount of the adsorbed gas in the gaseous mixture.

The electrolyte is a carbon dioxide rejecting, acid solution containing an anion which when adsorbed on the surface of the measuring electrode (anode), suppresses reduction of reductible gases, such as oxygen, but does not interfere significantly with adsorption of the electroactive gaseous component to be measured, for example, CO.

In preferred embodiments, the anion is dodecachloro-closododecaborate, $B_{12}Cl_{12}^{2-}$, provided in the form of the acid, commonly called chloroclosoborane, dissolved in a sulfuric acid electrolyte. Alternatively, hydrochloric acid may be substituted for the chloroclosoborane acid.

Further, in preferred embodiments, the electrochemical cell further comprises a reference electrode, and the applying and cycling of the potential involves correcting the measurement of the predetermined gas for background conditions by the steps of (a) initially maintaining the applied potential at a first potential level at which the gaseous mixture adsorbed on the anode is oxidized and a protective layer of oxide is formed on the anode, (b) reducing the applied potential to a second potential level at which the protective oxide is reduced, (c) maintaining the applied potential at the second potential level to permit the predetermined gas in the gaseous mixture to adsorb onto the anode at a rate which is diffusionally limited, (d) anodically sweeping the applied potential to a third potential level at which all of the adsorbed gaseous mixture is oxidized and measuring the current resulting from the potential sweep, the steps (a) through (d) constituting a measurement cycle, (e) repeating steps (a), (b), and (d), and (e) integrating the current resulting from the measurement cycle and the current resulting from the correction cycle, the difference in integrals being a measure of the amount of the predetermined gas, corrected for background conditions.

Further, in preferred embodiments the anode is a fuel cell type electrode on a support consisting of an intimate mixture of hydrophobic polymer and platinum catalyst deposited in a thin layer on a current conducting support, the electrolyte is in contact with the anode, the cathode is a fuel cell type electrode on a support in contact with the upper surface of a separator, the separator being saturated with the liquid electrolyte and having a lower surface and an upper surface, the separator overlying the anode and extending past the edges of the support of the anode such that the central portion of the lower surface is in contact with the anode, the separator having pores of size, size distribution, and overall volume so as to maintain a constant level of saturation of the liquid electrolyte on the anode, the reference electrode is a fuel cell type electrode on the support supporting the cathode and in contact with the upper surface of the separator, two porous hydrophobic polymer membranes, the first membrane underlying the anode and the second membrane overlying the cathode and the reference electrode, and the electrochemical cell further comprises a gas distribution screen underlying the first membrane and a housing.

Further, in preferred embodiments, the predetermined gas being measured is atmospheric CO, the anode is deposited in a thin layer on three current-conducting platinum wires and contains about $3 \times 10^{-2}$ mg platinum with a real platinum surface area of approximately 3 cm$^2$, the liquid electrolyte includes sulfuric and chloroclosoborane acids, the separator is a hydrophilic glass fiber separator, the housing is disc-shaped, the first potential level and the third potential level are both 1.8V vs. RHE, and the second potential level is 0.4V vs. RHE.

Several advantages are found in this invention. Oxidizing or reducing adsorbed materials on every cycle results in a clean, reproducible electrode surface. Drift is not of any consequence since the measurement of charge (integrated current) is immediately referred to the charge for the bare electrode. The method is sensitive, since materials accumulate over a long period of time relative to the time it takes to carry out the actual measurement. Since measurements are not absolute but relative, good accuracy can be achieved even if individual measurements are not accurate in an absolute sense since errors are generally reproducible and will cancel out. The same method can be used to measure gas concentrations ranging from a few parts per million (ppm) to a few thousand ppm by only adjusting the time allowed for adsorption. The cell can be used in the presence of oxygen since interference due to oxygen reduction at the adsorbing potentials is suppressed. The cell does not consume or accumulate any chemicals, since any oxygen reduced at the working electrode is evolved in the same quantity at the counter electrode.

Other features and advantages of the invention will be apparent from the following description of the preferred embodiments thereof, and from the claims.

We first briefly describe the drawings.

DESCRIPTION OF THE PREFERRED EMBODIMENT

Structure

Figure 1:
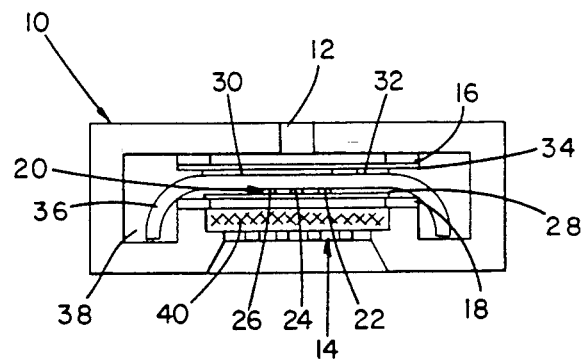
FIG. 1 is a diagrammatic cross-sectional view of an electrochemical cell.

The electrochemical cell (FIG. 1) is encased in a disc-shaped plastic housing 10, measuring approximately 2.5 cm (1 inch) in diameter and 0.5 cm ($\frac{1}{4}$ inch) in height. Communication with the ambient air is via breathing holes 12, 14 which open over porous hydrophobic polymer (Teflon (Goretex)) membranes 34, 28, respectively. These membranes have a negligible effect on gas transfer yet filter out dust and seal in liquid. The cell is thus completely sealed with respect to liquids and can be operated in any orientation.

Figure 2:
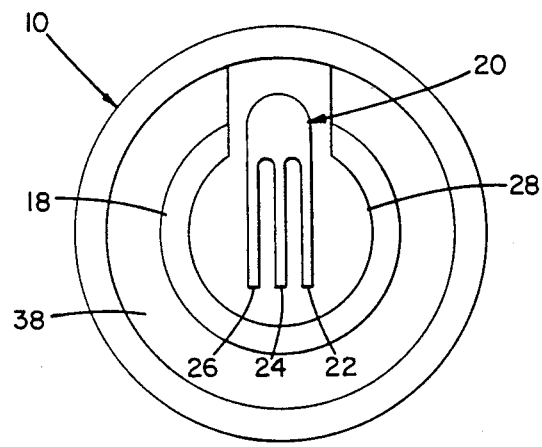
FIG. 2 is a diagrammatic plan view of the anode of the cell of FIG. 1.

The anode 20 is a gas diffusion type electrode containing a noble metal catalyst, preferably platinum, on which CO adsorbs and is electrochemically active, the catalyst being dispersed on a hydrophobic membrane. The structure of the anode is such that it is in contact with the electrolyte and the gaseous mixture. A fuel cell type electrode, including a platinum (Pt) catalyst intimately mixed with Teflon, also fulfills this requirement. The electrode consists of two interconnected networks: a hydrophilic network of Pt and a hydrophobic network of Teflon. There is a high area of contact between the catalyst phase, which is saturated with electrolyte, and the Teflon phase which is saturated with gas. The mixed hydrophilic-hydrophobic character of this electrode structure allows a very thin and dimensionally stable liquid film between the active electrode surface and the gas phase, through which the gas diffuses. The anode contains about $3 \times 10^{-2}$ mg Pt with a real Pt surface area of approximately 3 cm$^2$. Referring now to FIG. 2, the Pt Teflon mixture is deposited in a thin layer on three current conducting platinum wires 22, 24, 26, each of which is 0.008 cm wide and 0.5 cm long, which are supported on membrane 28.

Figure 3:
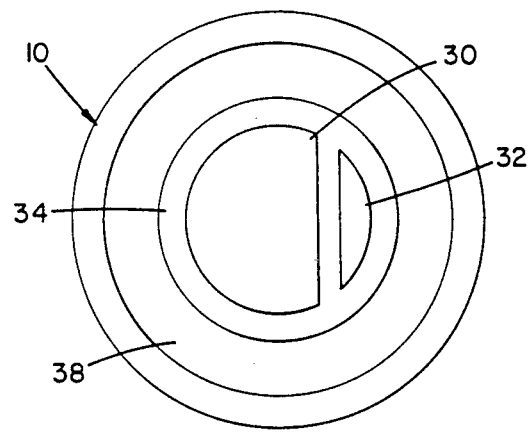
FIG. 3 is a diagrammatic plan view of the cathode and reference electrode of the cell of FIG. 1.

Referring to FIG. 3, fuel cell type electrodes are also used for both the cathode 30 and the reference electrode 32, which are both supported on membrane 34 (membrane 34 is in turn held on a support member 16). The cathode does not need to meet any specific performance parameters beyond being able to handle the cell currents without undue polarization. The reference electrode does not need to have a precisely defined reference potential since the measurement is a transient sweep and all potential steps, e.g., cleaning and adsorption, have a broad range. An air electrode, stable to 50–100 mV even in the presence of CO, is sufficient.

The electrolyte is comprised of an aqueous solution of sulfuric (or phosphoric) acid as the major component and chloroclosoborane acid, $H_2B_{12}Cl_{12}$, as a second component. The concentration of the sulfuric acid may vary from 0.5 to 18 molar. In general the concentration of the sulfuric acid is approximately 5 molar. The concentration of $H_2B_{12}Cl_{12}$ may vary from 10 millimolar to a saturated solution. The concentration of a saturated solution of $H_2B_{12}Cl_{12}$ depends on the concentration of the sulfuric acid.

$B_{12}Cl_{12}{}^{2-}$ may be added to the aqueous sulfuric acid as the salt of a monovalent or bivalent cation, $M_nB_{12}Cl_{12}$, where M is a monovalent cation such as Li$^+$ and n is equal to 2 or M is a divalent cation such as Ca$^{2+}$ and n is equal to 1; or as a monoacid of the formula $MHB_{12}Cl_{12}$ where M is a monovalent cation such as Li$^{30}$.

Other anions which adsorb on the active catalyst of the sensing electrode causing a deactivation of the activity of the catalyst for the electroreduction of oxygen without preventing the adsorption of carbon monoxide may be substituted for the $B_{12}Cl_{12}{}^{2-}$ anion. These include the inorganic anions of the general formula $B_zX_z{}^{2-}$ where X is a halogen, e.g., chlorine (Cl), bromine (Br) or iodine (I) and z is equal to 10 or 12. Alternatively, the anion can be of the formula $X^-$ where X is either chlorine (Cl), bromine (Br), or iodine (I). Most generally, the strength of adsorption of the anion on the electrode catalyst is strong enough to resist displacement by oxygen but not so strong as to resist displacement by the gas to be measured.

Likewise sulfuric acid can be replaced by other strong acid electrolytes. These acids include phosphoric acid and trifluoromethanesulfonic acid.

Further, any combination of the above mentioned acids comprising one component which is a strong acid and a second component from the above mentioned adsorbable anions can be used. The actual composition of the electrolyte is selected to produce an electrolyte with physical properties, i.e., equilibrium water vapor pressures, diffusion coefficients, gas solubilities, etc., appropriate for contact with the gaseous mixture in contact with the sensing electrode.

Sulfuric acid volumes in equilibrium with ambient air of variable relative humidity change by a factor of two over a humidity range of 20 to 80 percent. The sample of the gas to be measured may be pretreated to adjust its relative humidity to a predetermined level or the volume fluctuations may be accommodated while maintaining a constant "wetness" or saturation level at the electrodes, by a special separator-wick system. Referring again to FIG. 1, a hydrophilic glass fibre separator 36 lies between anode 20 and cathode 30 and reference 32, and extends past the edges of support member 18 and porous membrane 28 into reservoir 38. Separator 36 has a smaller pore size in the compressed region between the electrodes; this region is saturated with electrolyte by capillary action. Excess electrolyte occupies the large pores in the uncompressed overhang region and the reservoir. By controlling the pore size, pore size distribution, and overall pore volume of the separator and the volume of sulfuric acid initially placed in the cell, a constant saturation level is maintained at the electrodes even though the overall electrolyte volume varies. Also, since the electrolyte is immobilized within the porous structure, the possibility of spillage is avoided and the cell will perform in any orientation.

A metal gas-distribution screen 40 underlies porous membrane 28 to evenly distribute the impinging air onto the anode.

Operation

Figure 4:
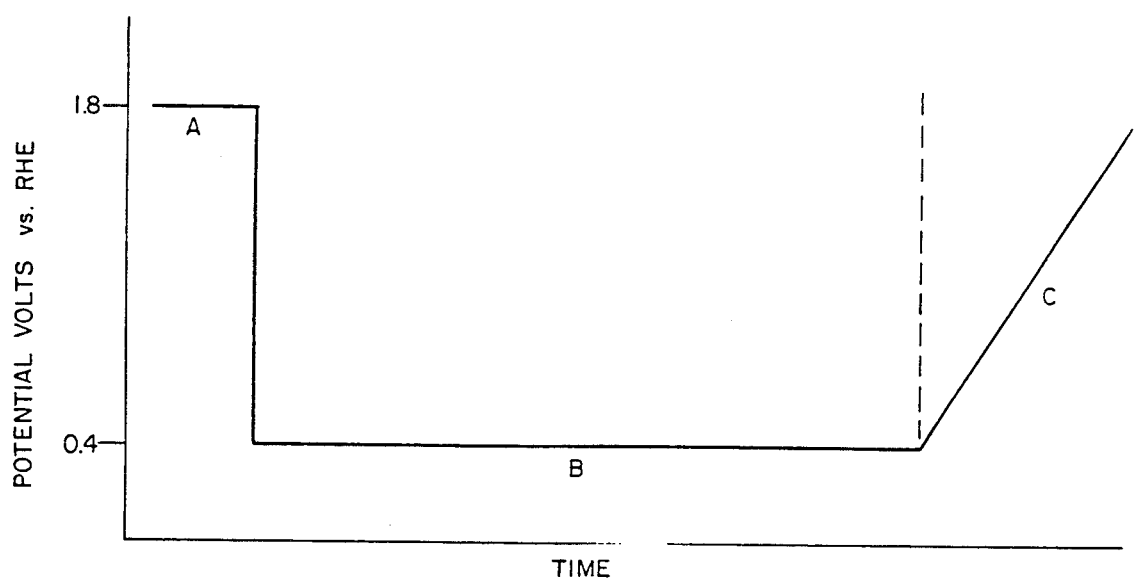
FIG. 4 is a graph illustrating the potential cycle applied to the cell of FIG. 1.
Figure 5:
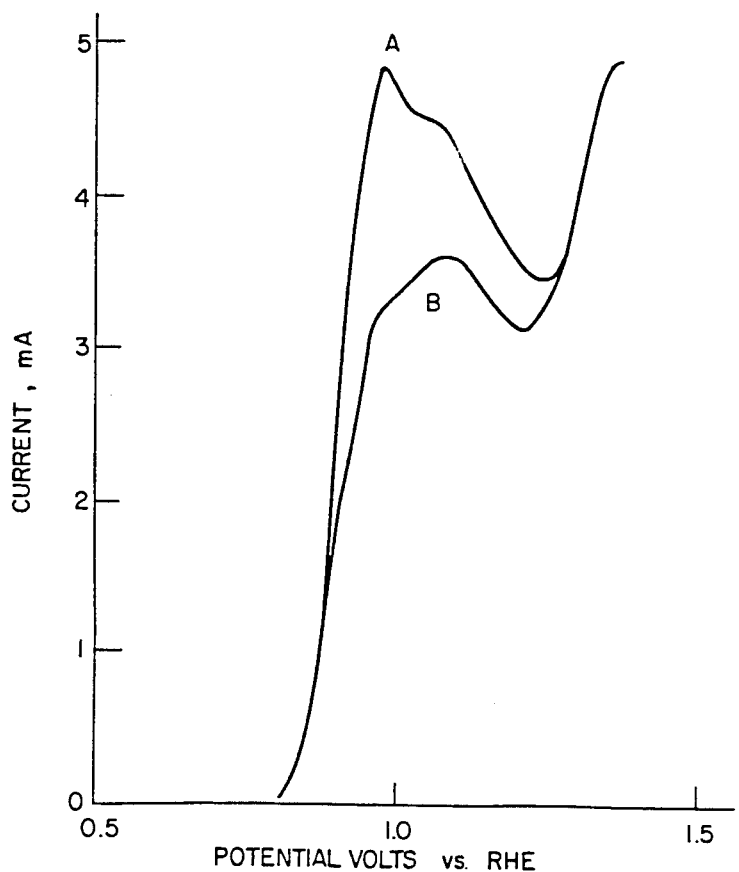
FIG. 5 is a graph of the current-potential curve for the anodic sweep portion of the measurement and correction cycles.

FIG. 4 illustrates the potential cycle applied in each of the measurement and correction cycles. The anode is first cleaned by maintaining the potential at a high level, approximately 1.8V vs. RHE (FIG. 4 at A), where all adsorbed material is removed and the surface becomes covered with a protective oxide layer. This oxide is then reduced at a low potential, e.g., 0.4V vs. RHE (FIG. 4 at B), resulting in a clean Pt surface. CO is then adsorbed onto the surface of the anode. During this time, the potential of the anode is maintained in a region where CO adsorption is diffusionally limited, e.g., 0.2 to 0.8V vs. RHE. The potential is then swept anodically (to more positive values) into the region of CO oxidation (FIG. 4 at C), while resulting current is measured. The cycle is then repeated without allowing time for CO adsorption. The amount of CO is proportional to the difference in anodic charge (current-time integral) between the first and second cycles. FIG. 5 shows the current-potential curves, A and B, for the first and second cycles, respectively. Alternatively, the amount of CO adsorbed can be determined from the oxidation current peak.

Other embodiments are within the following claims.
I claim:
1. A method for measuring the amount of a predetermined gas in a gaseous mixture using an electrochemical cell having a working electrode, a counter electrode, and an electrolyte, said method comprising
   contacting said gaseous mixture with said working electrode, and means for inhibiting the reduction of oxygen at said working electrode,
   adsorbing an anion on said working electrode sufficiently strongly to resist its own displacement by oxygen but not so strongly as to resist its own displacement by said predetermined gas,
   while said anion is adsorbed, applying a potential across said electrodes and cycling said applied potential, said cycling including an anodic sweep of said applied potential over a range between a potential level at which said predetermined gas in said gaseous mixture adsorbs onto said working electrode and a potential level at which said adsorbed predetermined gas is oxidized, said applied potential range including potentials at which oxygen is subject to reduction, and
   measuring the current resulting from said anodic sweep.

2. The method of claim 1 wherein said predetermined gas is CO.

3. The method of claim 2 wherein
   said working electrode is a fuel cell electrode on a support comprising an intimate mixture of hydrophobic polymer and platinum catalyst in contact with a current conducting wire,
   said electrolyte is a liquid in contact with said working electrode,
   said counter electrode is a fuel cell electrode on a support in contact with the upper surface of a separator, said separator being saturated with said liquid electrolyte and having a lower surface and an upper surface, said separator overlying said working electrode and extending past the edges of the support of said working electrode such that the central portion of said lower surface is in contact with said working electrode, said separator having pores of size, size distribution, and overall volume so as to maintain a constant level of saturation of said liquid electrolyte on said working electrode,
   said cell further comprises a reference electrode and said reference electrode is a fuel cell electrode on said support supporting said counter electrode and in contact with said upper surface of said separator,
   two porous hydrophobic polymer membranes, the first said membrane underlying said working electrode and the second said membrane overlying said counter electrode and said reference electrode, and
   said electrochemical cell further comprises
   a gas distribution screen underlying said first membrane, and
   a housing, 4. The method of claim 1 wherein
   said applying and cycling of said applied potential comprises correcting said measurement of said predetermined gas for background conditions by the steps of
   (a) initially maintaining said applied potential at a first potential level at which said gaseous mixture adsorbed on said working electrode is oxidized and a protective layer of oxide is formed on said working electrode, (b) reducing said applied potential to a second potential level at which said protective oxide is reduced, (c) maintaining said applied potential at said second potential level to permit said predetermined gas in said gaseous mixture to adsorb onto said working electrode, (d) sweeping said applied potential to a third potential level at which all of said adsorbed gaseous mixture is oxidized and measuring the current resulting from said potential sweep, said steps (a) through (d) comprising a measurement cycle, (e) repeating steps (a), (b), and (d), said steps (a), (b), and (d) comprising a correction cycle, and (f) integrating said current resulting from said measurement cycle and the current resulting from the potential sweep step of said correction cycle, the difference in integrals being a measure of said amount of said predetermined gas, corrected for background conditions.

5. The method of claim 1 wherein said anion is provided by a dissociable compound dissolved in said electrolyte.

6. The method of claim 5 wherein said dissociable compound is the acid of $(B_zX_z)^{-2}$, where B is boron, X is a halogen and z is equal to 10 or 12.

7. The method of claim 5 wherein said dissociable compound is hydrochloric acid.

8. The method of claim 1 wherein said anion is of the general formula $(B_zX_z)^{-2}$, where B is boron, X is a halogen, and z is equal to 10 or 12, or said anion is of the general formula $X_-$, where X is either chlorine, bromine, or iodine.

9. The method of claim 8, 6, or 7 wherein said electrolyte comprises sulfuric acid.

10. The method of claim 8, 6, or 7 wherein said electrolyte comprises phosphoric acid.

* * * * *

UNITED STATES PATENT AND TRADEMARK OFFICE
CERTIFICATE OF CORRECTION

PATENT NO. : 5,064,516

DATED : November 12, 1991

INVENTOR(S) : Martin W. Rupich

It is certified that error appears in the above-indentified patent and that said Letters Patent is hereby corrected as shown below:

Col. 4, line 59, "$Li^{30}$" should be --$Li^+$--.

Col. 6, lines 8-9, delete "and means for inhibiting the reduction of oxygen at said working electrode". (see amendment filed 6/18/90)

Col. 6, line 58, after "housing", delete "," and insert --.--.

Signed and Sealed this

Eighteenth Day of October, 1994

Attest:

BRUCE LEHMAN

Attesting Officer     Commissioner of Patents and Trademarks